(12) United States Patent
Miyazono et al.

(10) Patent No.: US 7,276,525 B2
(45) Date of Patent: Oct. 2, 2007

(54) OSTEOGENESIS-PROMOTION ENHANCER AND METHOD OF SCREENING THE SAME

(75) Inventors: Kohei Miyazono, Shiki (JP); Takeshi Imamura, Tokyo (JP); Shingo Maeda, Tokyo (JP)

(73) Assignee: Nippon Shinyaku Co. Ltd., Kyoto (JP)

( * ) Notice: Subject to any disclaimer, the term of this patent is extended or adjusted under 35 U.S.C. 154(b) by 0 days.

(21) Appl. No.: 10/559,155

(22) PCT Filed: Jun. 7, 2004

(86) PCT No.: PCT/JP2004/008248

§ 371 (c)(1),
(2), (4) Date: Mar. 13, 2006

(87) PCT Pub. No.: WO2004/108160

PCT Pub. Date: Dec. 16, 2004

(65) Prior Publication Data

US 2006/0183778 A1  Aug. 17, 2006

(30) Foreign Application Priority Data

Jun. 5, 2003  (JP) ............................. 2003-160354

(51) Int. Cl.
*A61K 31/44* (2006.01)
*A61K 38/00* (2006.01)

(52) U.S. Cl. .......................................... 514/341; 514/2
(58) Field of Classification Search ...................... None
See application file for complete search history.

(56) References Cited

U.S. PATENT DOCUMENTS 5,393,739 A * 2/1995 Bentz et al. .................. 514/12

FOREIGN PATENT DOCUMENTS

WO WO 00/61576 A1 10/2000
WO WO 02/22871 A2 3/2002

OTHER PUBLICATIONS

Fecik et al., "The Search for Orally Active Medications Through Combinatorial Chemistry", Res. Rev., 18, No. 3, 149-185, 1998.*
Kunio Takaoka, Tominaga Shimizu, "BMP ni yoru Hone Saisei to Kotsu Soshosho," Igaku no Ayumi, 2001, vol. 198, p. 625-629.
Spinella-Jaegle, S. et al., Opposite effects of bone morphogenetic protein-2 and transforming growth factor-beta1 on osteoblast differentiation, Bone, 2001, vol. 29, No. 4, p. 323-330.
Shingo Maeda, Kenji Imamura, Kohei Miyazono, "TGF-beta/BMP Signal to Kotsuga Saibo Bunka," Experimental Medicine, 2002, vol. 20, No. 17 (Zokan), p. 101-106.
Inman, Gareth J. et al., SB-431542 is a potent and specific inhibitor of transforming grown factor-beta superfamily type I activin receport-like kinase (ALK) recepotrs ALK4, ALK5, and ALK7, Molecular Pharmacology, 2002, vol. 62, No. 1, pp. 65-74.
S. Maeda, et al., Endogenous TGF-Beta Signaling Suppresses Maturation of Osteoblastic Mesenchymal Cells, The EMBO Journal, 2004, vol. 23, No. 3, 552-563.

* cited by examiner

*Primary Examiner*—Raymond J. Henley, III
(74) *Attorney, Agent, or Firm*—Dreier, LLP; Gerard F. Diebner

(57) ABSTRACT

It is an object of the present invention to provide an excellent enhancer for an osteogenesis accelerator that can enhance the activity of BMP as an osteogenesis accelerator. Another object of the present invention is to provide a method of screening for a novel enhancer for an osteogenesis accelerator.

The present invention relates to an enhancer for an osteogenesis accelerator, which comprises a compound having a TGF-β selective inhibitory activity as an active ingredient, the enhancer being administered with an osteogenesis accelerator containing BMP as an active ingredient either simultaneously or sequentially, and to a method of screening for an enhancer for an osteogenesis accelerator, comprising using a TGF-β inhibition as a measure for discovering the enhancer.

3 Claims, 8 Drawing Sheets

OSTEOGENESIS-PROMOTION ENHANCER AND METHOD OF SCREENING THE SAME

TECHNICAL FIELD

The present invention relates to an enhancer for an osteogenesis accelerator, which comprises a compound having a TGF-β (transforming growth factor-β) selective inhibitory activity as an active ingredient, and to a method of screening for an enhancer for an osteogenesis accelerator, comprising using a TGF-β inhibition as a measure for discovering the enhancer.

BACKGROUND ART

An osteogenesis accelerator is one of drugs which have been desired with the progression of the aging society in recent years, and as the accelerator, BMP (bone morphogenetic protein) or the like has been clinically used at present. However, the treatment with BMP has a problem that a satisfactory effect can not be obtained since any self regulatory mechanism acts on an osteogenetic activity of BMP. Although the cause of this has not been elucidated, the rapid disappearance of BMP from a grafted site, a negative feedback mechanism and the presence of an endogenous inhibitory substance have been considered as the cause [e.g., see Takase M et al., "Biochem Biophys Res Commun." published by Elsevier Science (U.S.A.), 1998, vol. 244, p. 26-29 and Valentin-Opran A et al., "Clin Orthop." published by Lippincott Williams & Wilkins (U.S.A.), 2002, vol. 395, p. 110-120].

BMP was discovered as a factor inducing heterotopic osteogenesis by Urist in 1965 [e.g., see Urist M R, "Science" published by American Association for the Advancement of Science (U.S.A.), 1965, vol. 150, p. 893]. Thereafter, DNA loning of human BMP succeeded [e.g., see Wozney J M et al., "Science" published by American Association for the Advancement of Science (U.S.A.), 1988, vol. 242, p. 1528-1534], which made it possible to produce recombinant human BMP (rhBMP). Accordingly, BMP has been clinically applied in the expectation that the bone defect would be efficiently repaired for a shorter period of time. BMP is one of molecules belonging to the TGF-β superfamily, and it has been known to accelerate chondrogenesis, fat formation and osteogenesis and to inhibit muscle formation from mesenchymal stem cells [e.g., see Katagiri T et al., "J. Cell Biol." published by Rockefeller University Press (U.S.A.), 1994, vol. 127, p. 1755-1766; Ahrens Metal., "DNA Cell Biol." published by Mary Ann Liebert inc. publishers (U.S.A.), 1993, vol. 12, p. 871-880 and Asahina I et al., "Exp. Cell Res." published by Elsevier Science (U.S.A.), 1996, vol. 222, p. 38-47].

TGF-β has been known to have an activity of controlling growth and differentiation of various cells including fibroblasts which are main cells constituting fibrous tissues and an activity of controlling the production and deposition of extracellular matrices indispensable for wound healing. Meanwhile, an activity of TGF-β on bones is unclear in many points, and there are reports stating that TGF-β acts positively on osteogenesis [e.g., see Erlebacher A et al., "J. Cell. Biol." published by Rockefeller University Press (U.S.A.), 1996, vol. 132, p. 195-210 and Alliston T et al., "EMBO J." published by Oxford University Press (England), 2001, vol. 20, p. 2254-2272] and reports stating that TGF-β acts negatively thereon [e.g., see Noda M et al., "Endocrinology" published by Endocrine Society (U.S.A.), 1989, vol. 124, p. 2991-2994 and Joyce M E et al., "J. Cell Biol." published by Rockefeller University Press (U.S.A.), 1990, vol. 110, p. 2195-2207].

DISCLOSURE OF THE INVENTION

It is an object of the present invention to provide an excellent enhancer for an osteogenesis accelerator, which can enhance the activity of BMP as an osteogenesis accelerator. Another object of the present invention is to provide a method of screening for a novel enhancer for an osteogenesis accelerator.

The present inventors have assiduously studied on osteogenesis. As a result, they have found that a compound having a TGF-β selective inhibitory activity enhances the osteogenesis-accelerating activity of BMP, and have completed the present invention.

The present invention can include, for example, the followings.

(1) An enhancer for an osteogenesis accelerator, which comprises a compound having a TGF-β selective inhibitory activity as an active ingredient, the enhancer being administered with an osteogenesis accelerator containing BMP as an active ingredient either simultaneously or sequentially.

(2) The enhancer for an osteogenesis accelerator according to (1), wherein the compound having a TGF-β selective inhibitory activity is 4-(4-benzo[1,3]dioxol-5-yl-5-pyridin-2-yl-1H-imidazol-2-yl)benzamide (hereinafter referred to as "compound A").

(3) A method of screening for an enhancer for an osteogenesis accelerator, comprising using a TGF-β inhibition as a measure for discovering the enhancer.

(4) A method of screening for an enhancer for an osteogenesis accelerator, comprising using a TGF-β inhibition and a BMP inhibition as measures for discovering the enhancer.

The present invention is described in detail below.

In the present invention, the "TGF-β selective inhibitory activity" means that signal transduction based on a stimulus by TGF-β is selectively inhibited. Here the "selectively" means that the signal transduction based on a stimulus by TGF-β is predominantly inhibited over the signal transduction based on a stimulus by BMP. The selectivity of the inhibitory activity varies depending on experimental systems used, conditions and the like. It is preferable that the TGF-β inhibition is three times or more the BMP inhibition. More preferably it should be five times or more, and further preferably ten times or more.

More specifically, "selectively" means that an activity of inhibiting the type II receptor or type I (ALK 5) receptors associated with the signal transduction by TGF-β, or an activity of inhibiting phosphorylation of Smad 2/3 predominates over an activity of inhibiting the type II or type I (ALK 2/3/6) receptors associated with the signal transduction by BMP, or an activity of inhibiting phosphorylation of Smad 1/5/8.

Both TGF-β and BMP belong to the TGF-β superfamily, and their signal transduction mechanisms are also similar. In the present invention, the enhancer for an osteogenesis accelerator, which comprises a compound having a TGF-β selective inhibitory activity, exhibits a pharmaceutical effect by increasing the function of accelerating osteogenesis based on stimulation by BMP or the like. Accordingly, a compound or a drug having a TGF-β inhibitory activity together with a comparable BMP inhibitory activity can not attain the object of the present invention.

With respect to the "compound having a TGF-β selective inhibitory activity" in the present invention, compounds having any chemical structures can be included in the present invention as far as they have the said activity. For example, the compounds including compound A as described in WO 00/61576 pamphlet are known to have an activity of selectively inhibiting ALK 5. Other examples thereof can include triaryl imidazole derivatives (e.g., see WO 00/172737 pamphlet), pyridinyl imidazole derivatives (e.g., see WO 00/162756 pamphlet), imidazole cyclic acetal derivatives (e.g., see WO 02/55077 pamphlet), benzimidazole derivatives (e.g., see WO 00/240467 pamphlet), diaryl imidazole derivatives (for example, WO 02/40468 pamphlet), pyrazole derivatives (e.g., see WO 02/066462 pamphlet; WO 02/062794 pamphlet and WO 02/062787 pamphlet), thiazole derivatives (e.g., see WO 02/062753 pamphlet; WO 02/062776 pamphlet and WO 02/062793 pamphlet), triazole derivatives (e.g., see WO 00/240476 pamphlet) and anti-TGF-β neutralizing antibodies [e.g., see Cordeiro M F, "Current opinion in Molecular Therapeutics" published by BioMed Central Ltd (U.S.A.), 2003, vol. 5, p. 199-203]. Further examples thereof can include the compounds: 3-(pyridin-2-yl)-4-(7-ethoxyquinolin-4-yl)pyrazole, 3-(2-propylpyridin-6-yl)-4-(quinolin-4-yl)pyrazole, 3-(2-methylpyridin-6-yl)-4-(7-ethoxyquinolin-4-yl)pyrazole, 3-(pyridin-2-yl)-4-(quinolin-4-yl)pyrazole, 3-(2-methylpyridin-6-yl)-4-(6-trifluoromethoxyquinolin-4-yl)pyrazole, 3-(2-methylpyridin-6-yl)-4-(6-chloroquinolin-4-yl)pyrazole, 3-(2-methylpyridin-6-yl)-4-(7-chloroquinolin-4-yl)pyrazole, 3-(3-ethoxyphenyl)-4-(7-ethoxyquinolin-4-yl)pyrazole, 5-hydroxymethyl-3-(pyridin-2-yl)-4-(quinolin-4-yl)pyrazole, 5-(2-phenetyl)-3-(pyridin-2-yl)-4-(quinolin-4-yl)pyrazole, 3-(3-trifluoromethylphenyl)-4-(quinolin-4-yl)pyrazole, 3-(3-bromophenyl)-4-(7-methylquinolin-4-yl)pyrazole, 3-(2-methylpyridin-6-yl)-4-(4-hydroxyphenyl)pyrazole, 5-methyl-3-(2-methylpyridin-6-yl)-4-(4-fluorophenyl)pyrazole, 3-(2-ethylpyridin-6-yl)-4-(4-fluorophenyl)pyrazole, 3-(2-methylpyridin-6-yl)-4-(4-fluorophenyl)pyrazole, 3-(2-methylpyridin-6-yl)-4-(2,4-dichlorophenyl)pyrazole, 3-(2-methylpyridin-6-yl)-4-(3,4-difluorophenyl)pyrazole and 3-(pyridin-2-yl)-4-(4-fluorophenyl)pyrazole, presented in an academic society [e.g., see The society of "American Association for Cancer Research special conference in Cancer research The TGF-beta superfamily, Jan. 15-19, 2003 La Jolla, Calif.", Abstract book, No.B51].

The "BMP", in the present invention, refers to a protein of the BMP family including various subtypes of BMP and recombinant proteins thereof. Examples thereof can include BMP-2/3/4/5/6/7/8, GDF (growth-differentiation factor)-5/6/7 and recombinant proteins thereof and the like.

The "osteogenesis accelerator", in the present invention, means a drug which can accelerate differentiation and maturation of osteoblasts and the like and can accelerate formation of bone cells. It can include BMP such as rhBMP. The "enhancer for an osteogenesis accelerator" means a drug which can enhance the activity of an osteogenesis accelerator. The enhancer can be used as a drug which is employed in (1) treatment of periodontal diseases, (2) treatment of various types of fractures such as open tibia fracture with a high incidence of false joint formation, delayed fracture, fracture with many bone defects and fracture associated with osteoporosis, (3) various surgical operations such as filling of a defective bone after excision of bone tumors, spinal fusion, bone regeneration of a bone necrotic portion of idiopathic osteonecrosis of femur head, osteosynthesis following osteotomy, e.g., high tibia osteotomy applied to osteoarthritis of knee joints, osteoplasty in temporomandibular arthrosis or occlusal insufficiency, and osteoplasty in skull or facial bone deformity.

In the present invention, the "method of screening for an enhancer for an osteogenesis accelerator, comprising using a TGF-β inhibition as a measure" includes known methods such as a test for measuring an activity of inhibiting the type II or type I (ALK 5) receptors associated with the signal transduction of TGF-β and a test for measuring an activity of inhibiting phosphorylation of Smad2/3. Known examples thereof include a method for examining TGF-β-induced collagen production using an intracellular amount of [$^3$H] proline incorporated as an index [e.g., see Kahari V M et al, "J. Clin. Invest." published by American Society for Clinical Investigation (U.S.A.), 1990, vol. 86, p. 1489-1495], a reporter assay using a cell line having introduced therein a chimera plasmid in which a promoter region of type I procollagen $\alpha_2$ chain gene is linked with a luciferase gene [e.g., see Boast S et al, "J. Biol. Chem." published by American Society for Biochemistry and Molecular Biology (U.S.A.), 1990, vol. 265, p. 13351-13356], a [$^3$H]thymidine incorporation assay in which an activity of inhibiting cell growth by TGF-β is measured with Mv1Lu cells [e.g., see Nakaoka T et al, "J. Clin. Invest." published by American Society for Clinical Investigation (U.S.A.), 1987, vol. 100, p. 2824-2832], a method for examining the inhibition of cell growth by TGF-β [e.g., see Nakaoka T et al, "J. Clin. Invest." published by American Society for Clinical Investigation (U.S.A.), 1987, vol. 100, p. 2824-2832 and Ebisawa T et al, "J Cell Sci." published by the company of biologists Ltd (England), 1999, vol. 112, p. 3519-3527], a method for examining differentiation of NmuMg cells [e.g., see Piek E et al, "J Cell Sci." published by the company of biologists Ltd (England) 1999, vol. 112, p. 4557-4568), a luciferase assay using a TGF-β reporter [e.g., see Tada K et al, "Genes Cells." published by Blackwell Synergy (England), 1999, vol. 4, p. 731-741), a method for examining the expression of target gene PAI-1 [e.g., see Saitoh M et al, "J Biol. Chem." published by American Society for Biochemistry and Molecular Biology (U.S.A.), 1996, vol. 271, p. 2769-2775], a method for examining the receptor binding with a crosslinking method [e.g., see Imamura T et al, "Nature" published by nature publishing group (England), 1997, vol. 389, p. 622-626] and a western blotting using an anti-phosphorylated Smad 2/3 antibody [e.g., see Inman G J et al, "Mol Cell." published by American Society for Microbiology (U.S.A.), 2002, vol. 10, p. 283-294], but is not limited to the above methods.

A novel enhancer for an osteogenesis accelerator, which has a TGF-β inhibitory activity, can be discovered by using these screening methods.

Further, an even more useful novel enhancer for an osteogenesis accelerator, which has a TGF-β inhibitory activity and a less BMP inhibitory activity, can be discovered by using these screening methods in combination with a screening method using a BMP inhibition as an index, which will be described below.

In the present invention, the "method of screening for an enhancer for an osteogenesis accelerator, comprising using a BMP inhibition as a measure" includes known methods such as a test for measuring an activity of inhibiting the type II or type I (ALK 2/3/6) receptors associated with the signal transduction of BMP and an activity of inhibiting phosphorylation of Smad 1/5/8. Known examples thereof include an assay of differentiation of mesenchymal stem cells (C2C12 cells and the like) to osteoblasts [e.g., see Fujii M et al, "Mol Biol Cell." published by American Society for Cell Biology (U.S.A.), 1999, vol. 10, p. 3801-3813], a luciferase assay using a reporter of BMP (1d-1-Luc) [e.g., see Korchynskyi O et al, "J Biol Chem." published by American Society for Biochemistry and Molecular Biology (U.S.A.), 2002, vol. 277, p. 4883-4891], a luciferase assay using a reporter of BMP (3GC-Luc) [e.g., see Ishida W et al, "J Biol Chem." published by American Society for Biochemistry and Molecular Biology (U.S.A.), 2000, vol. 275, p. 6075-6079], a luciferase assay using a reporter of BMP (GCCG-Luc) [e.g., see Kusanagi K et al, "Mol Biol Cell." published by American Society for Cell Biology (U.S.A.), 2000, vol. 11, p. 555-565], a method for measuring an mRNA expression of a target gene (1d-1 and the like) by real-time PCR [e.g., see Locklin R M et al, "J Bone Miner Res." published by American Society for Bone and Mineral Research (U.S.A.), 2001, vol. 16, p. 2192-2204], a secondary axis formation test using Xenopus [e.g., see Gyo Murakami, Tetsuro Watabe, Kunio Takaoka, Kohei Miyazono, and Takeshi Imamura, "Cooperative Inhibition of BMP Signaling by Smurf1 and Inhibitory Smads." MBC in Press, published Apr. 4, 2003 as 10.1091/mbc.E02-07-0441], a method for examining the receptor binding with a crosslinking method [e.g., see Imamura T et al, "Nature" published by nature publishing group (England), 1997, vol. 389, p. 622-626] and a western blotting using an anti-phosphorylated Smad 1/5/8 antibody [e.g., see Inman G J et al, "Mol Pharmacol." published by The American Society for Pharmacology and Experimental Therapeutics (U.S.A.), 2002, vol. 62, p. 65-74], but is not limited to the above methods.

Although an experiment by the method of screening of the present invention is itself well known, the present inventors have found for the first time that the method of screening can be used for the discovery of an enhancer for an osteogenesis accelerator.

BEST MODE FOR CARRYING OUT THE INVENTION

Figure 1:
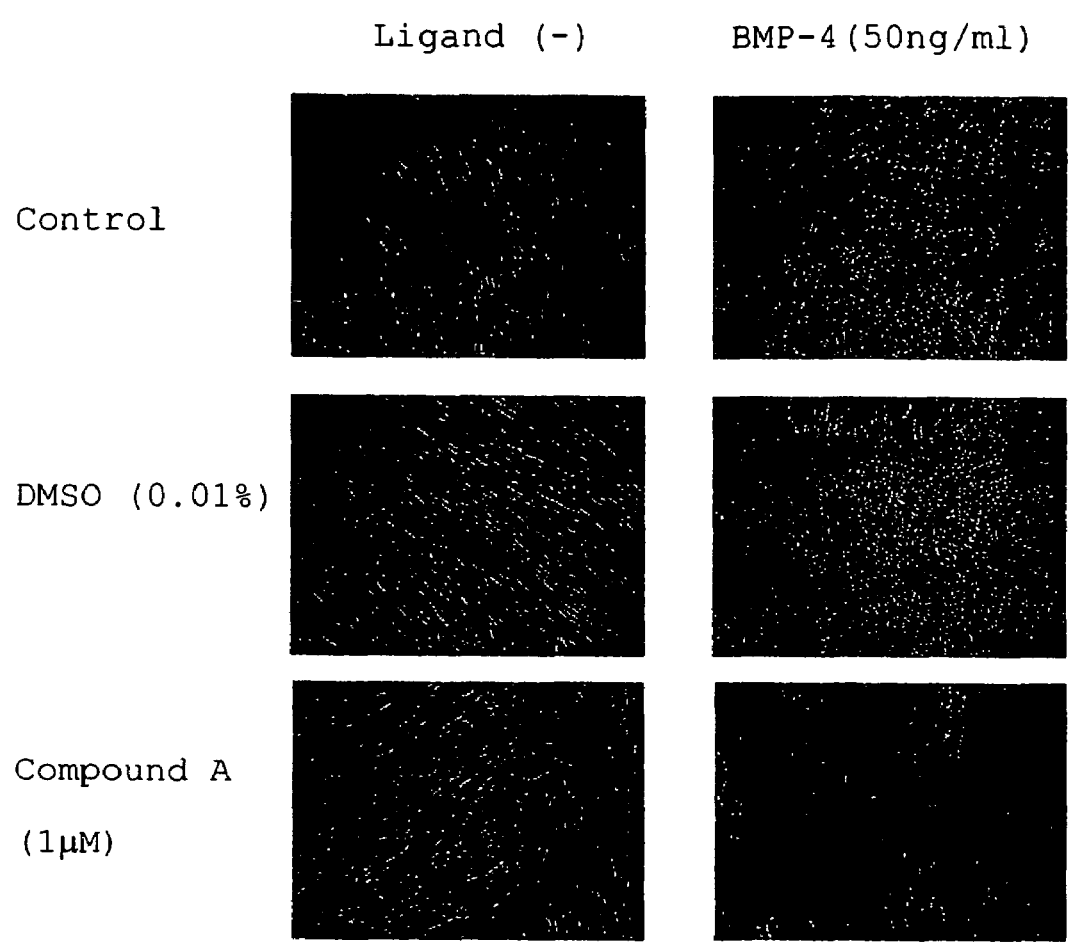
FIG. 1 is a photographic view of C2C12 cells stained with alkaline phosphatase in Test Example 1. The left column is a group without addition of rhBMP-4, and the right column is a group with addition of rhBMP-4. The upper part is a control group, the middle part is a group with addition of DMSO, and the lower part is a group with addition of compound A.

Among compounds having a TGF-β selective inhibitory activity, compounds having an acidic group can be used as a drug in the form of a free acid, and they may be used in the form of pharmaceutically acceptable salts according to a known method. Examples of such salts can include salts of alkali metals such as sodium and potassium, salts of alkaline earth metals such as calcium, and the like.

Among compounds having a TGF-β selective inhibitory activity, compounds having a basic group can be used as a drug in the form of a free base, and they may be used in the form of pharmaceutically acceptable salts according to a known method. Examples of such salts can include salts of mineral acids such as hydrochloric acid, hydrobromic acid, sulfuric acid and phosphoric acid, and salts of organic acids such as acetic acid, citric acid, tartaric acid, maleic acid, succinic acid, fumaric acid, p-toluenesulfonic acid, benzenesulfonic acid and methanesulfonic acid.

The compound having a TGF-β selective inhibitory activity can be administered with BMP either simultaneously or sequentially.

In the simultaneous administration, they may be administered as separate drugs simultaneously, or the compound having a TGF-β selective inhibitory activity or its pharmaceutically acceptable salt and BMP may be contained in a single pharmaceutical preparation. The sequential administration means that the compound having a TGF-β selective inhibitory activity or its pharmaceutically acceptable salt and BMP are administered at a prescribed time interval. In the present invention, either of them may be administered first. The prescribed time interval can be determined in consideration of kinetics of the osteogenesis accelerator used and the enhancer for it, and the like.

The drug according to the present invention is administered to animals including humans either as such or as a pharmaceutical composition in which the drug in a dose of, for example, from 0.01 to 99.5%, preferably from 0.5 to 90%, is contained in a pharmaceutically acceptable, non-toxic or inactive carrier.

As the carrier, one or more of a solid, semi-solid or liquid diluent, filler and other aids for formulation are used. It is advisable that the drug is administered in a unit dosage form. The drug can be administered by intravenous administration, oral administration, intra-tissue administration, local administration (percutaneous administration or the like) or transrectal administration, but is not limited to these administrations. Of course, the drug is administered in the dosage forms appropriate for these administration methods.

It is advisable to determine the dose of the enhancer for an osteogenesis accelerator in consideration of the character and degree of progression of diseases and wounds, the conditions of patients such as the age and body weight, the route of administration and the like. As an amount of an active ingredient in the drug of the present invention per adult, it is usually from 0.1 to 1,000 mg/person, preferably from 1 to 500 mg/person per day.

In some cases, a dose which is lower than the foregoing range is sufficient, or the dose is required to be rather higher than the foregoing range. It may be administered in 2 to 4 divided portions per day.

The oral administration can be performed in a solid or liquid dosage form such as powders, powder preparations, tablets, sugar coatings, capsules, granules, suspensions, liquid preparations, syrups, drops, sublingual tablets or the like.

A powder is prepared by milling the drug to an appropriate fine size. A powder preparation is prepared by milling the drug to an appropriate fine size and mixing it with a carrier for medical use which is likewise milled, for example, edible carbohydrates such as starch and mannitol and the like. A flavor, a preservative, a dispersing agent, a coloring agent, an aroma and the like may be incorporated as required.

A capsule is prepared by filling the above-formed powder or power preparation or granules to be described in the column of tablets into a shell of a capsule such as a gelatin capsule. A filling procedure may be conducted after mixing a milled substance with a lubricant and a fluidizing agent such as colloidal silica, talc, magnesium stearate, calcium stearate and solid polyethylene glycol. When a disintegrating agent and a solubilizing agent such as carboxymethylcellulose, calcium carboxymethylcellulose, hydroxypropylcellulose with a low degree of substitution, cross carmellose sodium, sodium carboxymethylstarch, calcium carbonate and sodium carbonate are added, the effectiveness of a drug ingested in the form of a capsule can be improved.

It is possible that a fine powder of a drug is suspended and dispersed in polyethylene glycol, glycerin and a surfactant and the dispersion is covered with a gelatin sheet to form a soft capsule. A tablet is produced by forming a powder mixture upon addition of an excipient, granulating or slugging the mixture, adding a disintegrating agent or a lubricant and then compressing the product. A powder mixture may be formed by mixing an appropriately powdered drug with the foregoing diluent or base and, as required, using also a binder (for example, sodium carboxymethylcellulose, methylcellulose, hydroxypropylmethylcellulose, gelatin, polyvinyl pyrrolidone and polyvinyl alcohol), a dissolution retarder (for example, paraffin), a reabsorber (for example, a quaternary salt) and an adsorbent (for example, bentonite, kaolin and dicalcium phosphate). It is possible that the powder mixture is first wetted with a binder such as syrup, starch paste, gum arabic, a cellulose solution or a polymer solution, then mixed by stirring, dried and granulated to form granules. Instead of such a granulation of the powder, it is also possible that the powder is first subjected to a compressor and the resulting incomplete slug is pulverized to form granules.

The thus-formed granules are mixed with a lubricant such as stearic acid, stearate salt, talc or mineral oils, making it possible to prevent mutual adhesion thereof. The thus-lubricated mixture is then compressed. The thus-formed crude tablets may be subjected to film coating or sugar coating.

The drug may be directly compressed after being mixed with a fluid inactive carrier without passing through the foregoing granulating or slugging step. A transparent or semitransparent protective coating made of a shellac closed film, a sugar coating, a coating of a polymeric material, or a polished coating made of wax is also available.

Another oral dosage form such as a solution, syrup or an elixir is converted to a unit dosage form in which a prescribed amount of a drug is incorporated. Syrup is produced by dissolving the drug in an appropriate aqueous flavor solution, and an elixir is produced using a non-toxic alcoholic carrier. A suspending agent is used by suspending the drug in a non-toxic carrier. A solubilizing agent and an emulsifying agent (for example, ethoxylated isostearyl alcohols and polyoxyethylene sorbitol esters), a preservative, a flavor-imparting agent (for example, peppermint oil and saccharin) and the like can be added as required.

As required, microcapsulation is also possible in a unit dosage form for oral administration. In this dosage form, prolongation of a working duration or sustained release is also enabled by coating or embedding in a polymer, wax or the like.

The intra-tissue administration can be conducted using a liquid unit dosage form for subcutaneous, intramuscular or intravenous injection, such as a solution or a suspension. These are produced by suspending or dissolving a prescribed amount of a drug in a non-toxic liquid carrier adapted for injection, such as an aqueous or oily medium and then sterilizing the suspension or the solution. A non-toxic salt or salt solution may be added to make the injection solution isotonic. Further, a stabilizer, a preservative and an emulsifying agent may be used.

BMP has been used by being grafted on a site to be treated as a pharmaceutical preparation adsorbed on a carrier such as a biodegradable matrix or porous particles. The drug according to the present invention may be used by being adsorbed on the same or different carrier.

The rectal administration can be performed using a suppository formed by dissolving or suspending the drug in a low-boiling water-soluble or water-insoluble solid such as polyethylene glycol, cacao butter, semisynthetic fat and oil (for example, Witepsol, a registered trademark), higher esters (for example, myristyl palmitate) or a mixture thereof.

The present invention is illustrated more specifically below by referring to the following Test Examples and Pharmaceutical Preparation Examples. However, the present invention is not limited thereto.

TEST EXAMPLE 1

Activity of Enhancing the Acceleration of Osteogenesis with Compound A (1)

C2C12 cells (American Type Culture Collection) were cultured in Dulbecco's Modified Eagle's Medium (DMEM) containing 5% fetal bovine serum (control), the same medium containing 0.01% dimethyl sulfoxide (DMSO) [DMSO (0.01%)] and the same medium containing 1 µM of compound A [compound A (1 µM)] with or without addition of 50 ng/ml of recombinant human BMP-4 (rhBMP-4). After the respective cells were cultured for 9 days, a degree of progression of bone differentiation was examined by staining with an alkaline phosphatase (ALP) staining kit #85-3R (Sigma). Quantitative analysis of an ALP activity was conducted according to the Fujii et al. method (e.g., see Fujii M et al, "Mol Biol Cell." published by American Society for Cell Biology (U.S.A.), 1999, vol. 10, p. 3801-3813] by using a Sigma Fast p-nitrophenyl phosphate tablet set. A protein concentration of each extract was measured by a DC protein assay (Bio-Rad) using a bovine serum albumin as a standard substance.

Figure 2:
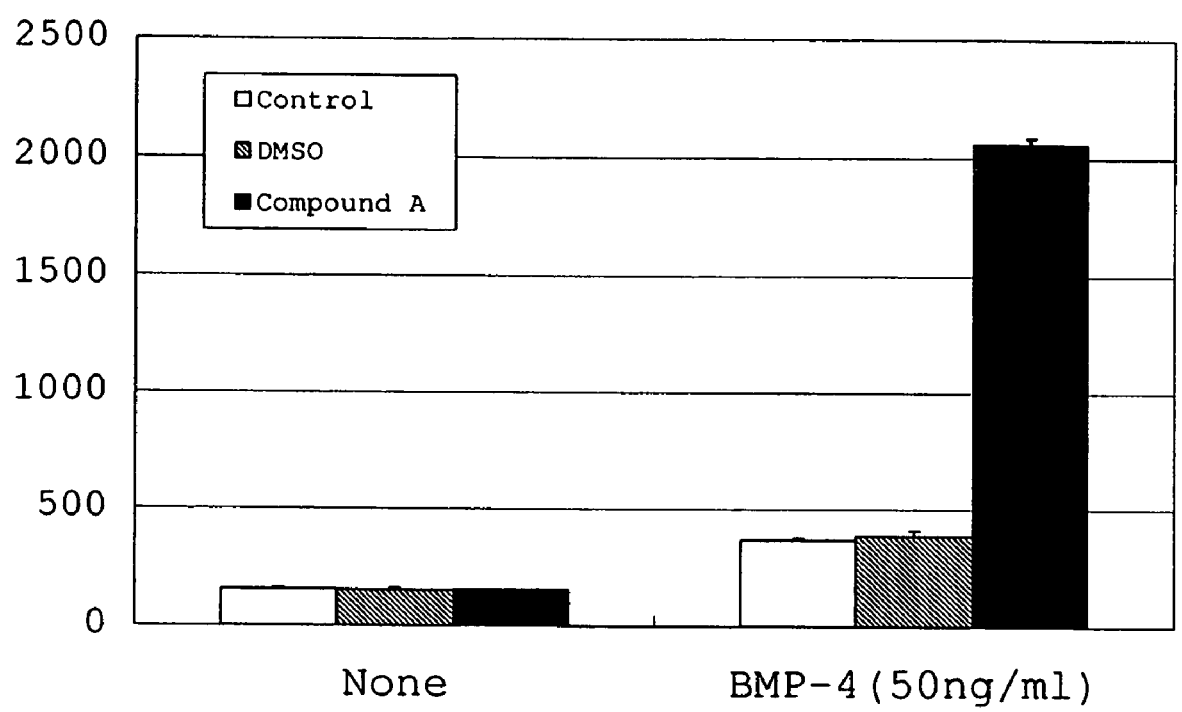
FIG. 2 is a graphical representation of an alkaline phosphatase activity of C2C12 cells in Test Example 1. The vertical axis indicates an alkaline phosphatase activity (nmol p-NP/min/mg protein).

The results are shown in FIGS. 1 and 2.

As shown in FIG. 1, an activity of accelerating bone differentiation of C2C12 cells was not observed with compound A alone. However, when bone differentiation of C2C12 cells were induced by rhBMP-4 (50 ng/ml), the activity of accelerating bone differentiation by stimulation of rhBMP-4 was enhanced by compound A.

TEST EXAMPLE 2

Activity of Enhancing the Acceleration of Osteogenesis with Compound A (2)

Human mesenchymal stem cells (hMSCs) (Poietics) were cultured in a serum-free medium containing an ITS supplement (Sigma), the same medium containing 0.01% DMSO [DMSO (0.01%)] and the same medium containing 1 µM of compound A [compound A (1 µM)] with or without addition of 50 ng/ml of rhBMP-4. Quantitative analysis of an ALP activity was conducted in the same manner as in Test Example 1. Accumulation of calcium was measured through visualization by the von Kossa method. That is, the respective cells were immobilized with a phosphate buffered saline (PBS) containing 3% glutaraldehyde, and washed with PBS and with distilled water. The immobilized cells were reacted with 2.5% silver nitrate for 60 minutes while applying light, then washed, and developed with 0.5% hydroquinone for 2 minutes. Excess silver was washed away with a 5% sodium thiosulfate solution.

Figure 3:
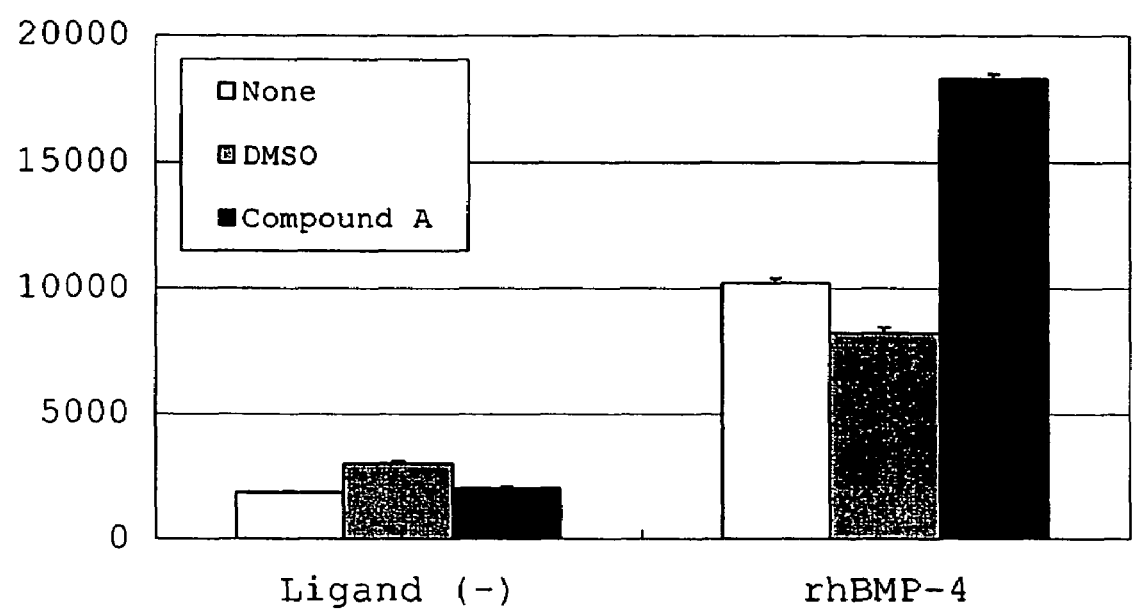
FIG. 3 is a graphical representation of an alkaline phosphatase activity of human mesenchymal stem cells in Test Example 2. The vertical axis indicates an alkaline phosphatase activity (nmol p-NP/min/mg protein).
Figure 4:
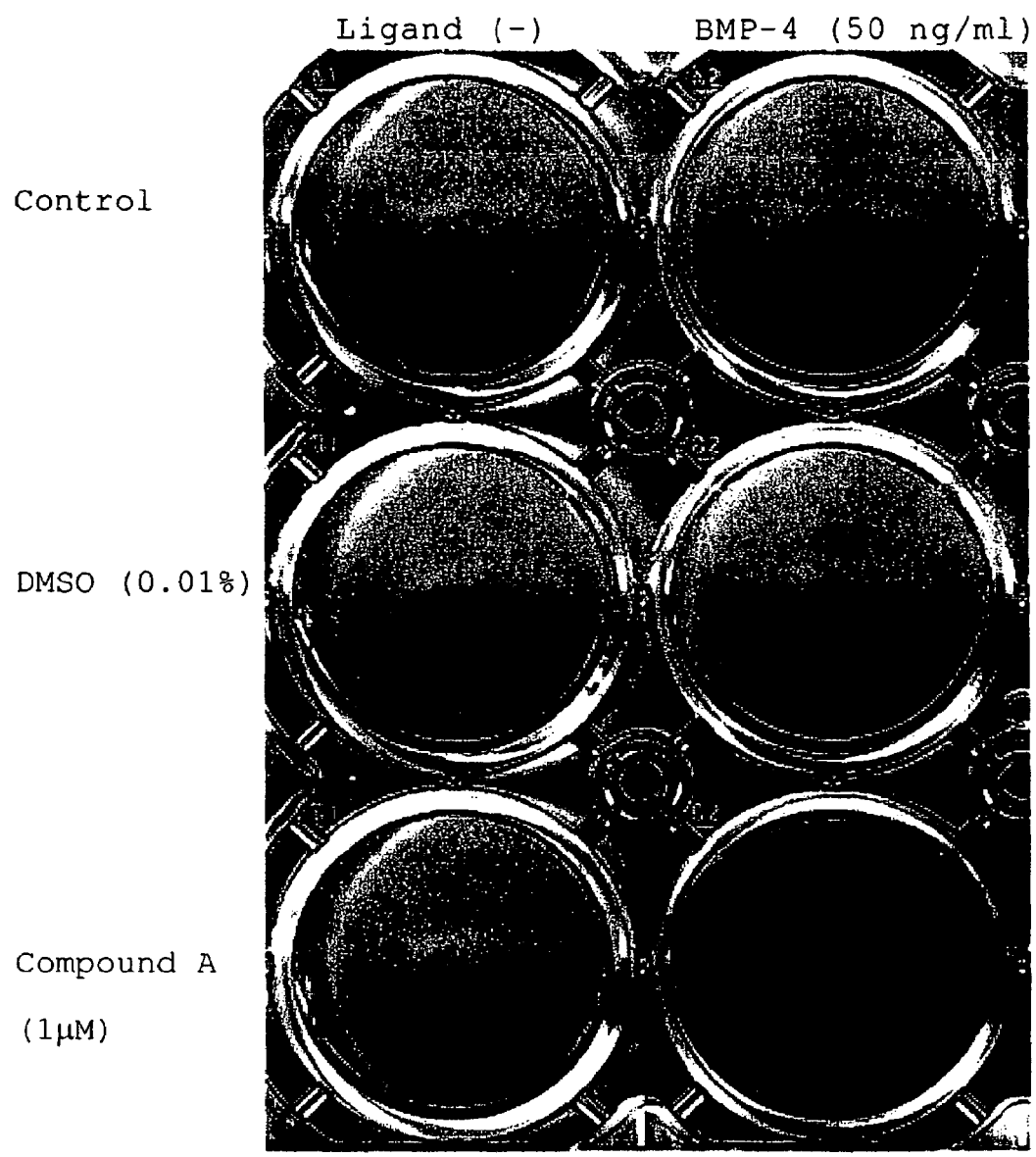
FIG. 4 is a photographic view of human mesenchymal stem cells subjected to von Kossa staining in Test Example 2. The left column is a group without addition of BMP-4, and the right column is a group with addition of BMP-4. The upper part is a control group, the middle part is a group with addition of DMSO, and the lower part is a group with addition of compound A.
Figure 5:
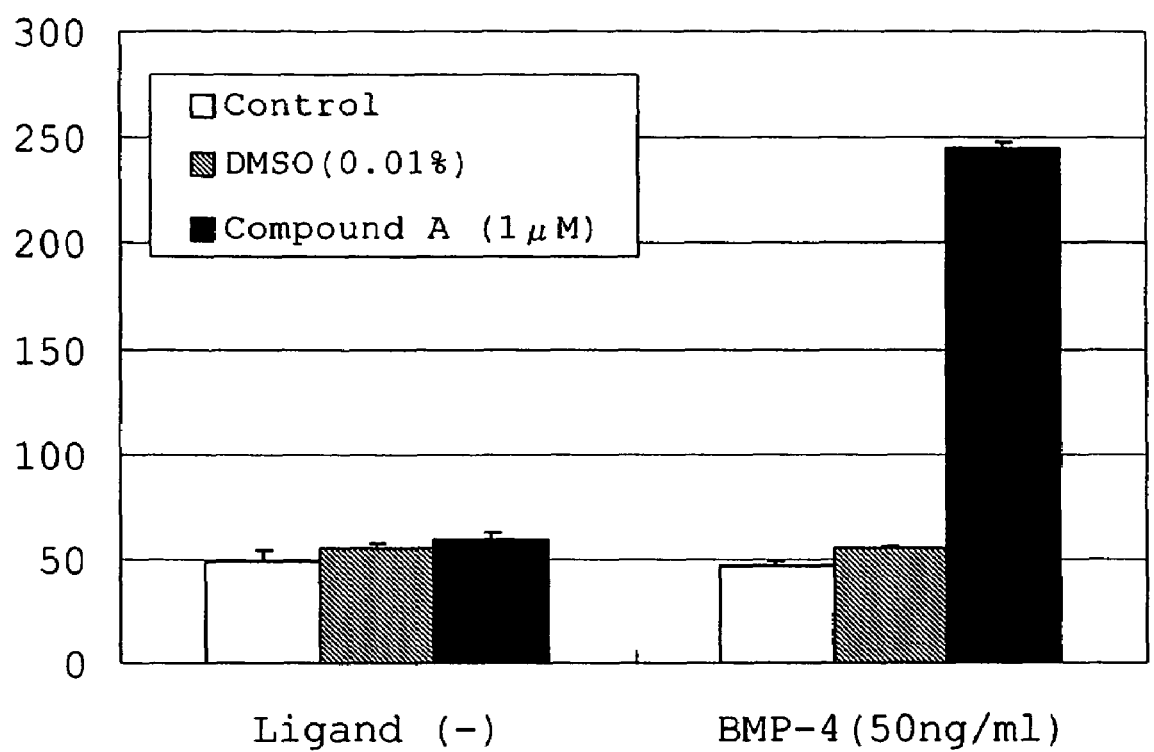
FIG. 5 is a graphical representation of the results of measuring human mesenchymal stem cells subjected to von Kossa staining with NIH image in Test Example 2.

The results are shown in FIGS. 3, 4 and 5.

As shown in FIGS. 3, 4 and 5, the increase in ALP activity and calcium accumulation induced with rhBMP-4 was further enhanced by addition of compound A. This also reveals that compound A enhances the activity of accelerating the bone differentiation by stimulation with rhBMP-4.

In order to make it clear that the activity of enhancing the acceleration of bone differentiation in Test Examples 1 and 2 is not based on the activity of compound A itself but is an activity caused by a TGF-β selective inhibition, the following Test Example 3 was conducted.

TEST EXAMPLE 3

Activity of Enhancing the Acceleration of Osteogenesis with an anti-TGF-β Neutralizing Antibody C2C12 cells were cultured for 9 days in a medium containing 50 ng/ml of rhBMP-4 and 10 µg/ml of an anti-TGF-β 1/2/3 neutralizing antibody, a medium containing 50 ng/ml of rhBMP-4, a medium containing 10 µg/ml of an anti-TGF-β 1/2/3 neutralizing antibody and a medium without addition thereof. Regarding the respective cells, an ALP activity was measured in the same manner as in Test Example 1.

Figure 6:
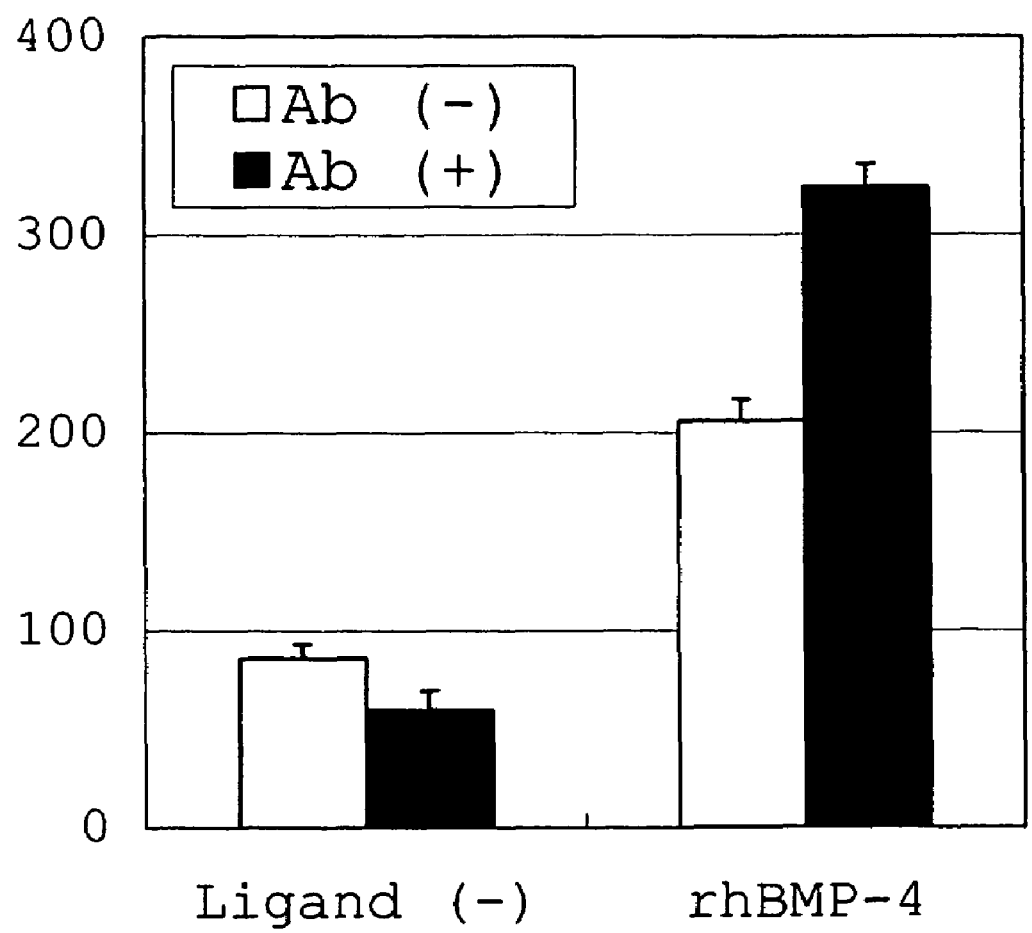
FIG. 6 is a graphical representation of an alkaline phosphatase activity of C2C12 cells in Test Example 3. The vertical axis indicates an alkaline phosphatase activity (nmol p-NP/min/mg protein).

The results are shown in FIG. 6.

As shown in FIG. 6, the anti-TGF-β neutralizing antibody (Ab) enhanced the activity of accelerating bone differentiation by stimulation with rhBMP-4 as in Test Example 1. The above results reveal that the activity of accelerating bone differentiation by BMP is enhanced by a TGF-β inhibition.

TEST EXAMPLE 4

Influence of a Serum Concentration on an Activity of Enhancing the Acceleration of Osteogenesis C2C12 cells were cultured for 9 days in a medium whose FBS concentration was adjusted to 2.5%, 5%, 10% or 20% in the presence of 1 µM of compound A and 50 ng/ml of rhBMP-4. As a control, C2C12 cells were cultured with addition of 0.01% DMSO instead of compound A or without addition thereof. Regarding the respective cells, the ALP activity was measured in the same manner as in Test Example 1.

Figure 7:
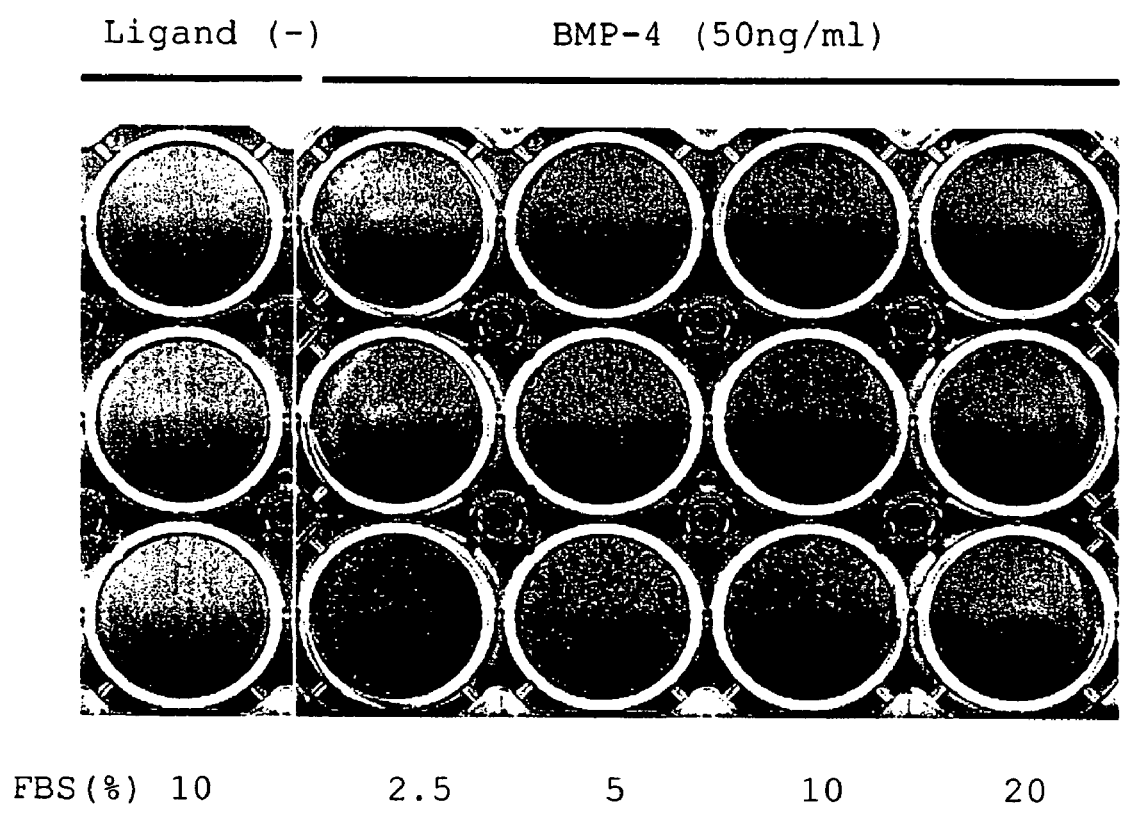
FIG. 7 is a photographic view of C2C12 cells stained with alkaline phosphatase in Test Example 4. The leftest column is a group with addition of 10% FBS and without addition of BMP-4, and the 2nd, 3rd, 4th and 5th columns from the left are groups with addition of 2.5, 5, 10 and 20% of FBS respectively and with addition of BMP-4. The upper part is a control group, the middle part is a group with addition of DMSO, and the lower part is a group with addition of compound A.
Figure 8:
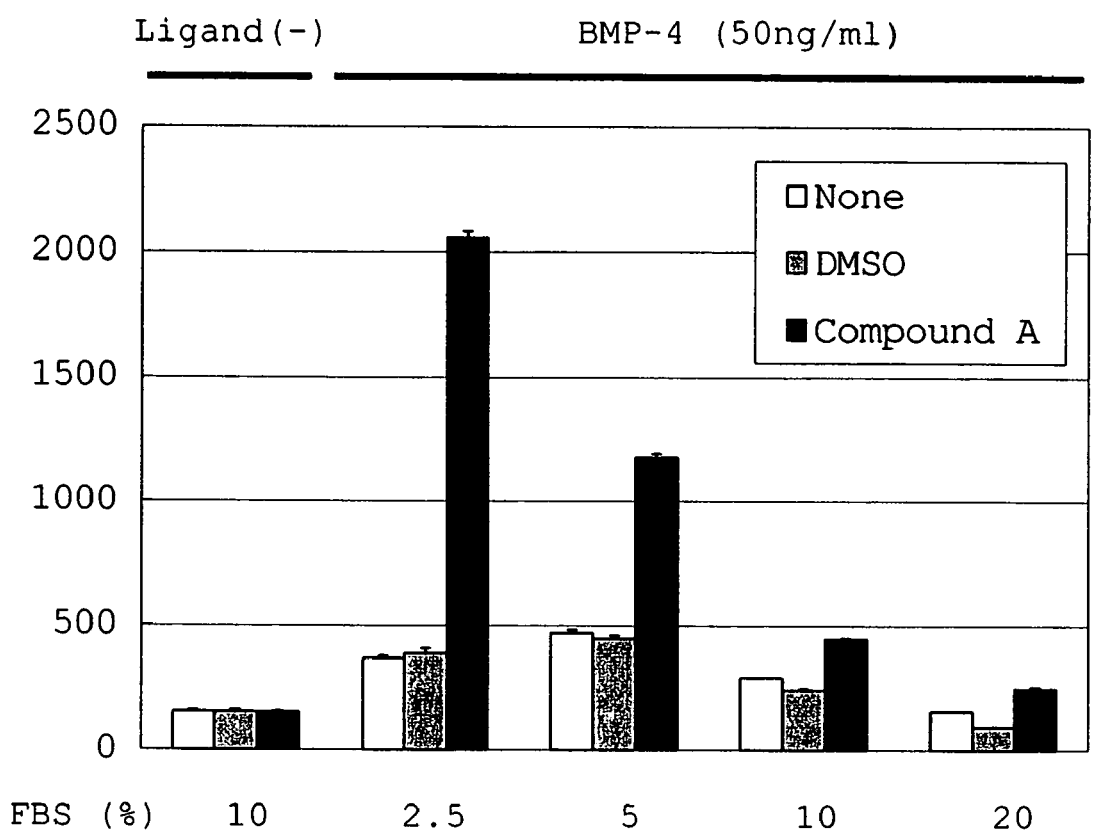
FIG. 8 is a graphical representation of an alkaline phosphatase activity of C2C12 cells in Test Example 4. The vertical axis shows an alkaline phosphatase activity (nmol p-NP/min/mg protein).

The results are shown in FIGS. 7 and 8.

As shown in FIGS. 7 and 8, the activity of compound A to enhance the acceleration of osteogenesis was decreased with the increase in FBS concentration. With respect to this phenomenon, it is considered, from the facts obtained in Test Examples 1 and 2, that the activity of enhancing the acceleration of osteogenesis is decreased with the increase in FBS concentration, namely the increase in TGF-β concentration in serum. From this fact as well, it is clear that compound A enhances the activity of BMP to accelerate osteogenesis by selectively inhibiting signal transduction by TGF-β.

PHARMACEUTICAL PREPARATION EXAMPLE 1

| Tablet (tablet for internal use) Recipe: In 80 mg of one tablet | |
|---|---|
| Compound A | 5.0 mg |
| Cornstarch | 46.6 mg |
| Crystalline cellulose | 24.0 mg |
| Methylcellulose | 4.0 mg |
| Magnesium stearate | 0.4 mg |

A powder mixture of this recipe is compressed in a conventional manner to form tablets for internal use.

PHARMACEUTICAL PREPARATION EXAMPLE 2

| Tablet (tablet for internal use) Recipe: In 80 mg of one tablet | |
|---|---|
| Compound A | 5.0 mg |
| Cornstarch | 46.6 mg |
| Crystalline cellulose | 24.0 mg |
| Methylcellulose | 4.0 mg |
| Magnesium stearate | 0.4 mg |

A powder mixture of this recipe is compressed in a conventional manner to form tablets for internal use.

INDUSTRIAL APPLICABILITY

The enhancer for an osteogenesis accelerator according to the present invention can enhance the activity of accelerating bone differentiation by simultaneous administration or sequential administration with an osteogenesis accelerator containing BMP. Accordingly, the higher usefulness in clinically using the BMP-containing osteogenesis accelerator can be expected. Further, a method of screening for the novel enhancer for an osteogenesis accelerator is provided which is useful for screening of clinically desired drugs.

The invention claimed is:

1. A method for enhancing an osteogenesis accelerating effect of a bone morphogenic protein (BMP), comprising the step of administering an effective amount of BMP to a human or other animal, and the step of administering a compound having a transforming growth factor-β (TGF-β)

selective inhibitory activity to said human or other animal, the steps being performed either simultaneously or sequentially.

2. The method of claim 1, wherein the compound having a TGF-β selective inhibitory activity is 4-(4-benzo[1,3]dioxol-5-yl-5-pyridin-2-yl-1H-imidazol-2-yl)benzamide.

3. A method of screening an enhancer for an osteogenesis accelerator, comprising the steps of:
   a) examining an osteogenesis accelerating effect of a bone morphogenetic protein (BMP),
   b) examining an osteogenesis accelerating effect of the bone morphogenetic protein (BMP) in combination with a compound having a transforming growth factor-β (TGF-β) inhibitory activity, and
   c) selecting the compound having a transforming growth factor-β (TGF-β) inhibitory activity used in step b), wherein the osteogenesis acceleration measured in the above step b) is higher than that of the step a).

* * * * *

UNITED STATES PATENT AND TRADEMARK OFFICE
CERTIFICATE OF CORRECTION

PATENT NO.         : 7,276,525 B2
APPLICATION NO.    : 10/559155
DATED              : October 2, 2007
INVENTOR(S)        : Kokei Miyazono, Takeshi Imamura and Shingo Maeda It is certified that error appears in the above-identified patent and that said Letters Patent is hereby corrected as shown below:

On the cover page, after "(75) Inventors: Kohei Miyazono, delete "Shiki" and insert therefore --Saitama--.

On the cover page, after "(73) Assignee: Nippon Shinyaku Co. Ltd, Kyoto (JP)" add --, Japanese Foundation for Cancer Research, Tokyo (JP)--

Signed and Sealed this
Seventeenth Day of April, 2012

David J. Kappos
*Director of the United States Patent and Trademark Office*